United States Patent [19]

McCall

[11] 4,073,296

[45] Feb. 14, 1978

[54] APPARATUS FOR ACUPRESSURE TREATMENT

[76] Inventor: Francis J. McCall, Box 236, Lansing, Ill. 60438

[21] Appl. No.: 646,003

[22] Filed: Jan. 2, 1976

[51] Int. Cl.[2] ...................... A61B 17/00; A61H 39/04

[52] U.S. Cl. ................................................ 128/303 R

[58] Field of Search .................. 128/1 R, 303 R, 329, 128/329 A

[56] References Cited

U.S. PATENT DOCUMENTS

| | | | |
|---|---|---|---|
| 737,473 | 8/1903 | Porter | 128/399 X |
| 2,163,792 | 6/1939 | Littlehales | 128/303 R |
| 3,675,642 | 7/1972 | Lord | 128/303 R |
| 3,900,018 | 8/1975 | Piunno | 128/303 R X |
| 3,923,064 | 12/1975 | Leupold | 128/329 A |

OTHER PUBLICATIONS

Young, Karl, "Tiny Staple in Ear Helps Reduce Weight or Smoking", in The National Bulletin, p. 6, May 26, 1975.

*Primary Examiner*—Channing L. Pace
*Attorney, Agent, or Firm*—Alter and Weiss

[57] ABSTRACT

An acupressure treatment device including a custom made ear mold having precisely located acupuncture nodules fixed thereto for depressing points on the ear which control or act upon the known auricular acupuncture points.

3 Claims, 5 Drawing Figures

Fig. 2
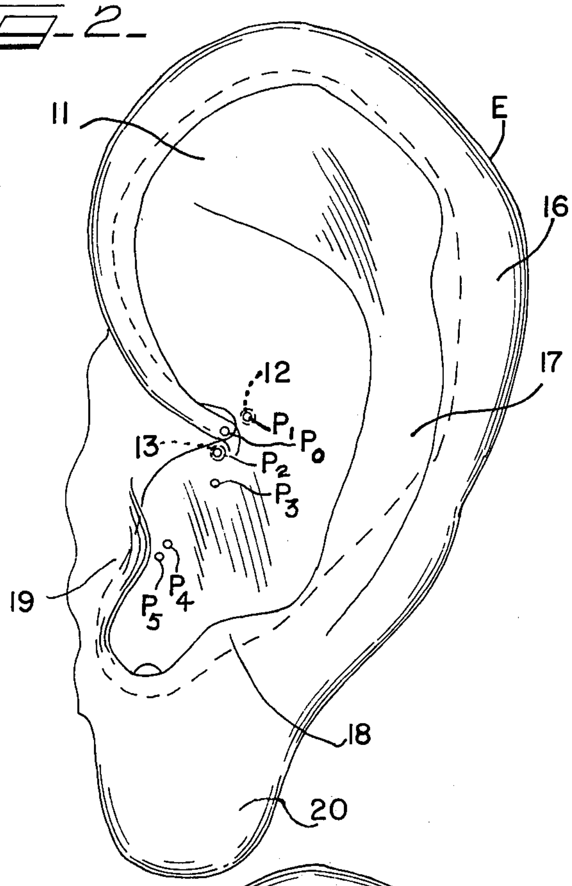
Fig. 5
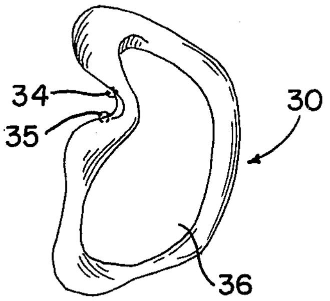
Fig. 1
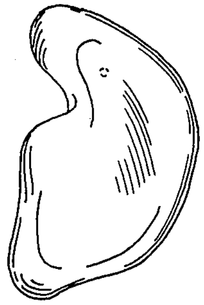
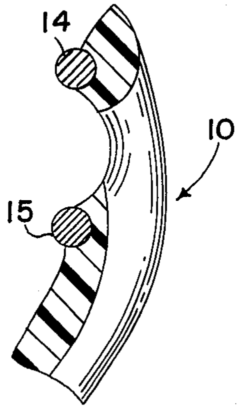
Fig. 4
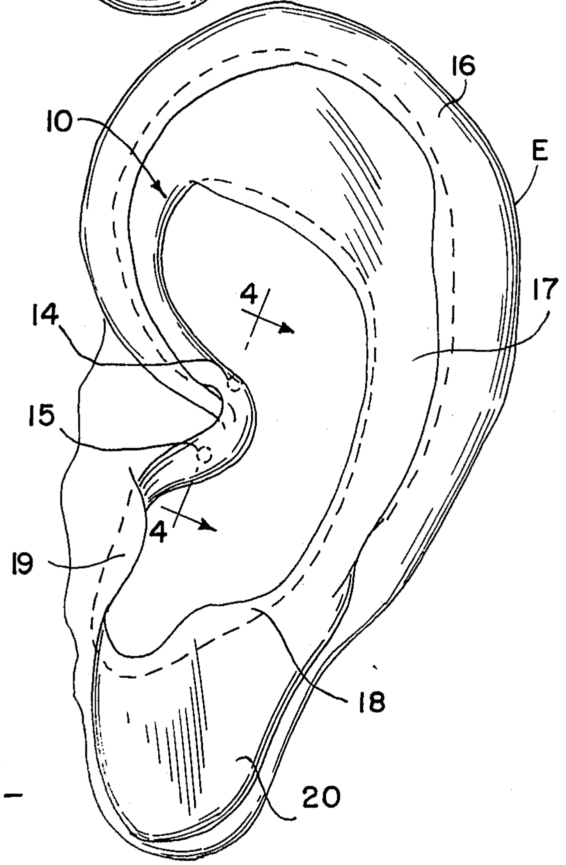
Fig. 3

APPARATUS FOR ACUPRESSURE TREATMENT

BACKGROUND AND SUMMARY OF THE INVENTION

The present invention relates to acupuncture therapy and more particularly to an acupressure device for practicing the therapy.

It is known that certain locations or acupuncture points on the ear when subject to acupuncture treatment affect or have a theraputic influence on corresponding body functions, reactions, muscles, organs, systems and the like. For example, one specific acupuncture point on the ear may influence throat action, another the mouth function, while still another stomach activity. Location and stimulation of these sensitive acupuncture points with acupuncture therapy has been used to treat such conditions as obesity, alcoholism, drug addiction, smoking and the like.

Heretofore, when treatment for any condition has been desired it has been necessary to have the treatment performed by an acupuncture practioner or a physician who pierced the skin and stimulated the acupuncture points with fine needles. This type of treatment of course is not always possible, since bodily cravings and desires and the concomitant need for treatment occur with no predictability and consequently the effectiveness of such treatment is dependant on the availability of skilled services when the patient is experiencing the urges and desires which are the subject of the treatment.

A technique is also known and in use in which a tiny metal staple, the size of the one used millions of times daily on letters, is injected into the smooth part of the ear and functions to stimulate the sensitive acupuncture points of the ear. The patient wiggles the metal staple to accomplish the desired theraputic result. However, this technique suffers from shortcomings in that the injection of the staple into the ear is usually accompanied by pain and the presence of a foreign body in the ear requires daily application of an antibiotic cream to the ear to prevent infection. Morever, the staple is permanently implanted in the ear and is visible to an onlooker.

By the present invention there is provided an acupressure device which eliminates the need for everyday services of an acupuncture practioner or physician and which may be inserted into the ear by the individual or patient to permit the patient to treat himself under the guidance and control of his physician. This is accomplished by an impression of the ear molded to conform to the patient's ear. An acupressure nodule, button or ion or series of acupressure nodules, buttons, or ions are precisely located on the ear mold opposite appropriate ear points to depress these points on the ear which correspond to the known acupuncture points of the body function being treated to obtain the desired theraputic result. The acupressure device may be removed by the patient after each treatment at any time or as instructed by the physician.

BRIEF DESCRIPTION OF THE DRAWINGS

FIG. 1 is an elevational view of the ear mold of the present invention.

FIG. 2 is an enlarged view of the impression used to form the ear mold of the present invention before removal from the ear of the patient being treated.

FIG. 3 is an enlarged elevational view of the ear mold shown in FIG. 1 inserted in the patient's ear during treatment.

FIG. 4 is a cross sectional view taken generally along the lines 4—4 of FIG. 3.

FIG. 5 is an elevational view of another embodiment of an ear mold made from the impression shown in FIG. 2.

More specifically FIGS. 2 and 4 show parts of the pinna of the ear: the helix 16, antihelix 17, antitragus 18, tragus 19 and the lobe 20.

DESCRIPTION OF THE PREFERRED EMBODIMENTS

Referring now to the drawings in particular in FIGS. 1–4 there is shown a solid ear mold 10 having acupressure nodules 14 and 15 inserted therein. The ear mold 10 is formed from either a clear hard lucite, i.e. methyl methacrylate; a soft lucite, i.e. ethyl methylacrylate or a non toxic plastic, i.e. an acrylic resin.

The ear mold 10 is formed by initially forming an impression 11. The impression 11 is made from a plastic material usually used for surgical purposes. To this end the plastic material is mixed with a suitable liquid and inserted into a syringe. Prior to introducing the mixture into the ear E, the auditory canal (not shown) of the ear is suitable plugged or blocked by cotton or the like to prevent the plastic material from entering the inner ear.

The impression material is then inserted into the ear E by means of the syringe so that the auditory canal is originally filled. The syringe is then slowly withdrawn and the bowl and helix areas of the ear E are filled. Thereafter the material is tapped with a finger so as to eliminate any lines or air pockets. Further impression material is added to fill the bowl area, helix, tragus and other parts of the ear E. The material is again lightly firmed to eliminate any further lines or air pockets. During firming care should be taken not to distort the ear E.

After the plastic material has set the impression 11 is removed from the ear by pressing the edges of the ear back and away from the impression. The impression 11 is rotated slowly and easily to break and separate it from the skin on the ear. At the same time the impression 11 is extracted from the helix curl and thereafter pulled out normal to the ear. The cotton block or plug is removed from the ear E by tweezers. Care must be taken that all of the cotton is removed from the canal.

After the impression 11 is formed as described above the acupuncture points of treatment are selected. As known the ear E has a number of sensitive acupuncture points designated P1, P2, P3, etc., which act upon and influence various body members and functions when stimulated. These points are generally located relative to each other and to a zero reference point, P0. The zero point, P0, is located on the helix 16 of ear as shown in FIG. 2.

These points are charted on an auricular anatomical chart of the ear. Other exemplifying points are also shown located on the ear E. It should be understood that not all of the known points are illustrated.

Assuming it is desired to treat an individual or patient for alcoholism, the acupuncture points P1, P2, etc. on the ear E which affect or influence this function are located. This is accomplished by using the auricular anatomical chart to approximately locate these acupuncture points. To ascertain the precise location a known standard auricular electrical point locater is used. The zero point, P0, is first located with one probe of the locater and when the acupuncture point P1, is located which acts upon or influences the body member or function to be treated a buzzing or humming sound is emitted by the instrument. Similarly a second acupuncture point P2, and any desired additional acupuncture points are located which affect the body function to be influenced.

The acupuncture points P1 and P2 thusly located in the ear are marked or spotted with a surgical ink pen. The plastic impression is then reinserted into the ear E so that the surgical ink spots 12 and 13 will be transferred to the impression 11 and leave imprints thereon. The imprinted impression 11 is then removed from the ear E and then inserted into a casting or forming mold from which the ear mold is cast. The surgical ink spots 12 and 13 are transferred from the impression 11 to the forming mold. On the forming mold at the location of the transferred ink spots, indentations are formed to accomodate acupressure nodules, buttons or ions used to stimulate the body function to be treated. The nodules 14 and 15 may be spherical in shape and may be made of gold, silver, steel, copper, platinum, plastic or rubber. The size of the nodule will vary depending on the therapy or treatment being applied and will measure no less than about 1 millimeter in diameter. The nodules 14 and 15 are inserted in the forming mold in the indentations prior to casting the ear mold 10. The ear mold 10 is then formed by pouring the liquid lucite or plastic material into the finished forming mold. At this time, the nodules 14 and 15 are encaptured in the solidifying ear mold 10 and located precisely at the proper location to affect the desired treatment when the ear mold 10 is inserted in the ear E.

Treatment is accomplished under the direction of a physician by merely inserting the ear mold 10 into the ear E and pressing on the ear mold 10 with a finger. The acupressure nodules 14 and 15 will apply a mild pressure at the precise acupuncture points which act on and influence the body member or function being treated. When relief or the treatment is completed the ear mold 10 may readily be removed and reinserted under the direction of a physician whenever needed by the patient without requiring medical or technical assistance. This is particularly helpful in the treatment of such conditions as obesity, alcoholism, drug addiction, smoking and the like. Whenever the urge is present to consume food, alcohol, drugs or to smoke, depressing or wiggling the ear mold 10 having the precisely aligned nodule 14 and 15 affixed thereto will stimulate or affect the proper acupuncture points to eliminate or control the urge and thus provide relief.

Referring now to FIG. 5 there is shown another embodiment of the present invention, an ear mold 30 in the general shape of a ring having acupressure nodules 34 and 35 molded therein. The ear mold 30 is formed in a similar manner to the solid ear mold 10.

The ear mold 30 is molded to conform to the shape of the ear E to maintain the nodules 34 and 35 aligned with the appropriate acupuncture points of the ear. The ear mold 30 is provided with an opening or aperture 36 to permit sound waves to enter the ear E and to minimize possible ear infection and irritation due to the lucite or acrylic compound in the ear mold.

From the foregoing, the construction, manufacture and operation of the acupressure treatment device will be readily understood and further explanation is believed to be unnecessary. However, since numerous modifications and changes will readily occur to those skilled in the art, it is not desired to limit the invention to the exact constructions shown and described, and accordingly, all suitable modifications and equivalents may be resorted to, falling with the scope of the appended claims.

What is claimed is:

1. An acupressure treatment device comprising:
a plastic mold conforming to a human external ear,
said mold adapted to be removably retained in said ear in a predetermined position, relative to acupuncture points located in the ear and influencing corresponding specific body functions to be treated; and
nodule means embedded in said plastic mold,
said nodule means not less than about one millimeter in diameter,
said nodule means positioned on said mold to depress at least one of said specific acupuncture points and thereby treat said corresponding body function, when said mold is retained in said predetermined position in said ear.

2. The apparatus as recited in claim 1 wherein said nodule means are spherical in shape.

3. The apparatus as recited in claim 1 wherein said mold includes a plurality of said nodule means positioned to depress selected of said acupuncture points.

* * * * *

REEXAMINATION CERTIFICATE (108th)

United States Patent [19]
McCall

[11] B1 4,073,296
[45] Certificate Issued Jul. 19, 1983

[54] APPARATUS FOR ACUPRESSURE TREATMENT

[76] Inventor: Francis J. McCall, Box 236, Lansing, Ill. 60438

Reexamination Request

No. 90/000,195, May 4, 1982

Reexamination Certificate for:

| | |
|---|---|
| Patent No.: | **4,073,296** |
| Issued: | **Feb. 14, 1978** |
| Appl. No.: | **646,003** |
| Filed: | **Jan. 2, 1976** |

[51] Int. Cl.³ .......................... A61B 17/00; A61H 39/04

[52] U.S. Cl. ............................ 128/303 R; 128/329 A

[58] Field of Search ............. 128/329 A, 303 R, 907; 264/222, Dig. 30

[56] References Cited

U.S. PATENT DOCUMENTS

| | | | |
|---|---|---|---|
| 737,473 | 8/1903 | Porter | 128/399 X |
| 1,971,630 | 8/1934 | Von Suchorzynski. | |
| 2,163,792 | 6/1939 | Littlehales | 128/303 R |
| 3,675,642 | 7/1972 | Lord | 128/303 R |
| 3,900,018 | 8/1975 | Piunno | 128/303 R X |
| 3,923,064 | 12/1975 | Leupold | 128/329 A |
| 4,037,590 | 7/1977 | Dohring et al. | 128/329 A X |

FOREIGN PATENT DOCUMENTS

| | | |
|---|---|---|
| 127274 | 6/1947 | Australia. |

OTHER PUBLICATIONS

"Acupuncture and the Ear", by Dr. Grace Dohring (Ref. DERMA-PATCHES), 1974.

"Acupuncture: 5000 years of Healing Art," by R. Czaplicki, 1975.

Young, Karl, "Tiny Staple In Ear Helps Reduce Weight Or Smoking", the National Bulletin, page 6, May 26, 1975. 128/329 A.

*Primary Examiner*—M. H. Thaler

[57] ABSTRACT

An acupressure treatment device including a custom made ear mold having precisely located acupuncture nodules fixed thereto for depressing points on the ear which control or act upon the known auricular acupuncture points.

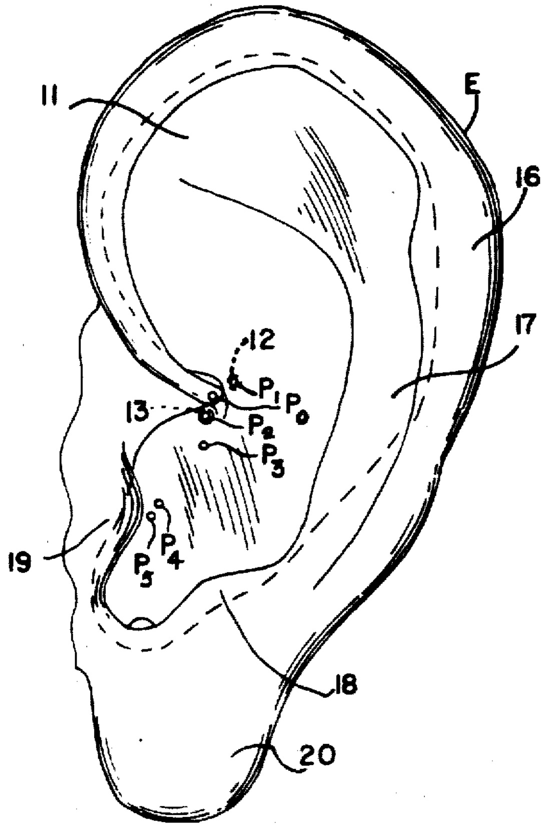

REEXAMINATION CERTIFICATE ISSUED UNDER 35 U.S.C. 307.

THE PATENT IS HEREBY AMENDED AS INDICATED BELOW.

Matter enclosed in heavy brackets appeared in the patent, but has been deleted and is no longer a part of the patent; matter printed in italics indicates additions made to the patent.

AS A RESULT OF REEXAMINATION IT HAS BEEN DETERMINED THAT:

The patentability of claims 1–3 is confirmed.

New claims 4 and 5 are added and determined to be patentable.

*4. An acupressure treatment device comprising:*

*a plastic mold closely conforming to a human external ear, said plastic mold to be locatable in a predetermined position and only in this said predetermined position within the external ear;*

*said mold to be removably retained within said external ear in said predetermined position, said mold to be located directly adjacent acupuncture points located within said external ear which are to influence corresponding specific body functions to be treated; and*

*nodule means imbedded within said plastic mold, said nodule means to contact said external ear, said nodule means not less than about one millimeter in diameter, said nodule means positioned on said mold to depress at least one of said acupuncture points and thereby treat at least one said corresponding specific body function when said mold is retained in said predetermined position in said ear.*

*5. The acupressure treatment device of claim 4 wherein:*

*said nodule means comprising a plurality of spaced-apart nodules, each said nodule to depress on a said separate acupuncture point.*

* * * * *